(12) United States Patent
Guo et al.

(10) Patent No.: US 9,983,205 B2
(45) Date of Patent: May 29, 2018

(54) MICROFLUIDIC DEVICES FOR AUTOMATED ASSAYS

(71) Applicant: Bio-Rad Laboratories, Inc., Hercules, CA (US)

(72) Inventors: Kun Guo, Hercules, CA (US); Young Joon Kim, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 349 days.

(21) Appl. No.: 14/689,791

(22) Filed: Apr. 17, 2015

(65) Prior Publication Data
US 2015/0301033 A1   Oct. 22, 2015

Related U.S. Application Data

(60) Provisional application No. 61/981,617, filed on Apr. 18, 2014.

(51) Int. Cl.
*B01L 3/00* (2006.01)
*G01N 33/543* (2006.01)
(Continued)

(52) U.S. Cl.
CPC .. *G01N 33/54366* (2013.01); *B01L 3/502715* (2013.01); *B01L 7/52* (2013.01);
(Continued)

(58) Field of Classification Search
CPC .......... G01N 33/54366; B01L 3/502715; B01L 7/52; B01L 2200/027; B01L 2200/0621;
(Continued)

(56) References Cited

U.S. PATENT DOCUMENTS 4,963,498 A    10/1990  Hillman et al.
5,356,525 A    10/1994  Goodale et al.
(Continued)

FOREIGN PATENT DOCUMENTS

WO    2013106458    7/2013

OTHER PUBLICATIONS

European Patent Application No. EP15780234.9 , "Extended European Search Report", dated Oct. 7, 2016, 7 pages.
(Continued)

*Primary Examiner* — Erik B Crawford
(74) *Attorney, Agent, or Firm* — Kilpatrick Townsend & Stockton LLP

(57) ABSTRACT

Provided herein are cartridges, devices, and methods for carrying out multistep assays on a microfluidic scale. A cartridge includes a block frame comprising a well, wherein the well comprises an outlet, at least one inlet, and a bottom surface; a plurality of containers, wherein each container is connected to the well via a microchannel leading to the at least one inlet; and an openable cover, which cover when closed is configured to enclose an assay surface and form a gap between (i) the assay surface and the bottom surface of the well or (ii) the assay surface and the cover. The gap can be formed by a spacer that extends from the bottom surface of the well or from the outer edge of the cover. Methods include flowing liquid into the gap and/or through an opening adjacent to the assay surface.

12 Claims, 4 Drawing Sheets

(51) Int. Cl.
 *C12Q 1/68* (2018.01)
 *B01L 7/00* (2006.01)

(52) U.S. Cl.
 CPC ......... *C12Q 1/6834* (2013.01); *C12Q 1/6876* (2013.01); *B01L 2200/025* (2013.01); *B01L 2200/027* (2013.01); *B01L 2200/0621* (2013.01); *B01L 2300/043* (2013.01); *B01L 2300/047* (2013.01); *B01L 2300/0636* (2013.01); *B01L 2300/0819* (2013.01); *B01L 2300/0867* (2013.01); *B01L 2300/1822* (2013.01); *B01L 2400/049* (2013.01); *B01L 2400/0487* (2013.01)

(58) Field of Classification Search
 CPC ......... B01L 2300/043; B01L 2300/047; B01L 2300/0636; B01L 2300/0819; B01L 2300/0867; B01L 2300/1822; B01L 2400/0487; B01L 2400/049; C12Q 1/6834; C12Q 1/6876

See application file for complete search history.

(56) References Cited

U.S. PATENT DOCUMENTS

| | | |
|---|---|---|
| 5,399,486 A | 3/1995 | Cathey et al. |
| 2007/0166200 A1 | 7/2007 | Zhou et al. |
| 2007/0269893 A1* | 11/2007 | Blankenstein .... B01L 3/502723 436/2 |
| 2009/0320930 A1 | 12/2009 | Zeng et al. |
| 2010/0075311 A1 | 3/2010 | Barrault et al. |
| 2012/0142026 A1* | 6/2012 | Miller ................. B01L 3/50273 435/7.9 |
| 2012/0177543 A1* | 7/2012 | Battrell ............... B01F 11/0071 422/187 |
| 2012/0201723 A1 | 8/2012 | Bogen et al. |
| 2013/0071935 A1 | 3/2013 | Bergman et al. |
| 2013/0134040 A1 | 5/2013 | Lee et al. |
| 2013/0251604 A1 | 9/2013 | Kim et al. |
| 2014/0087359 A1* | 3/2014 | Njoroge ................. C12N 1/066 435/2 |

OTHER PUBLICATIONS

International Search Report and Written Opinion from PCT/US2015/026502, dated Jul. 8, 2015.
"BenchMark XT" brochure (2013) Ventana Medical Systems, Inc. (2 pages).
"IF Sprinter" brochure (2012) EuroImmuns US. (2 pages).

* cited by examiner

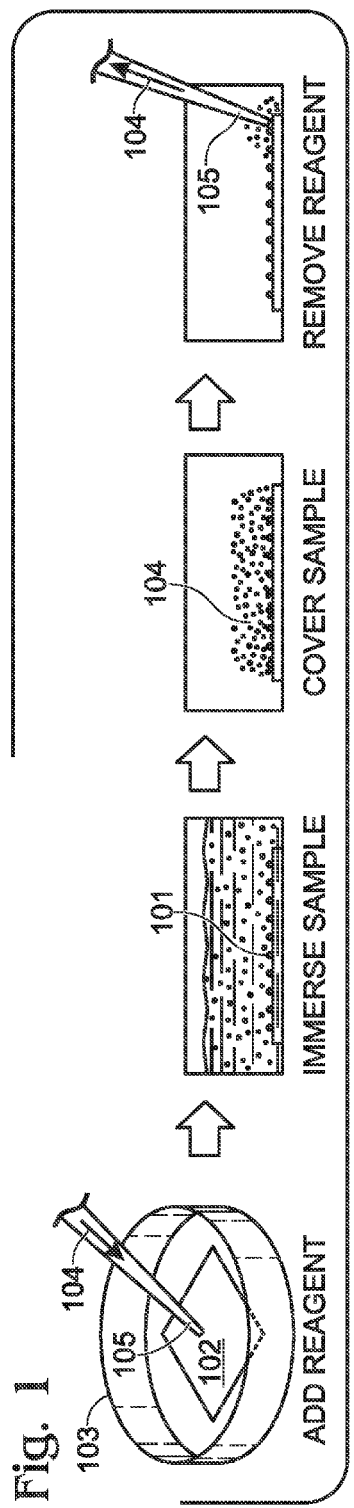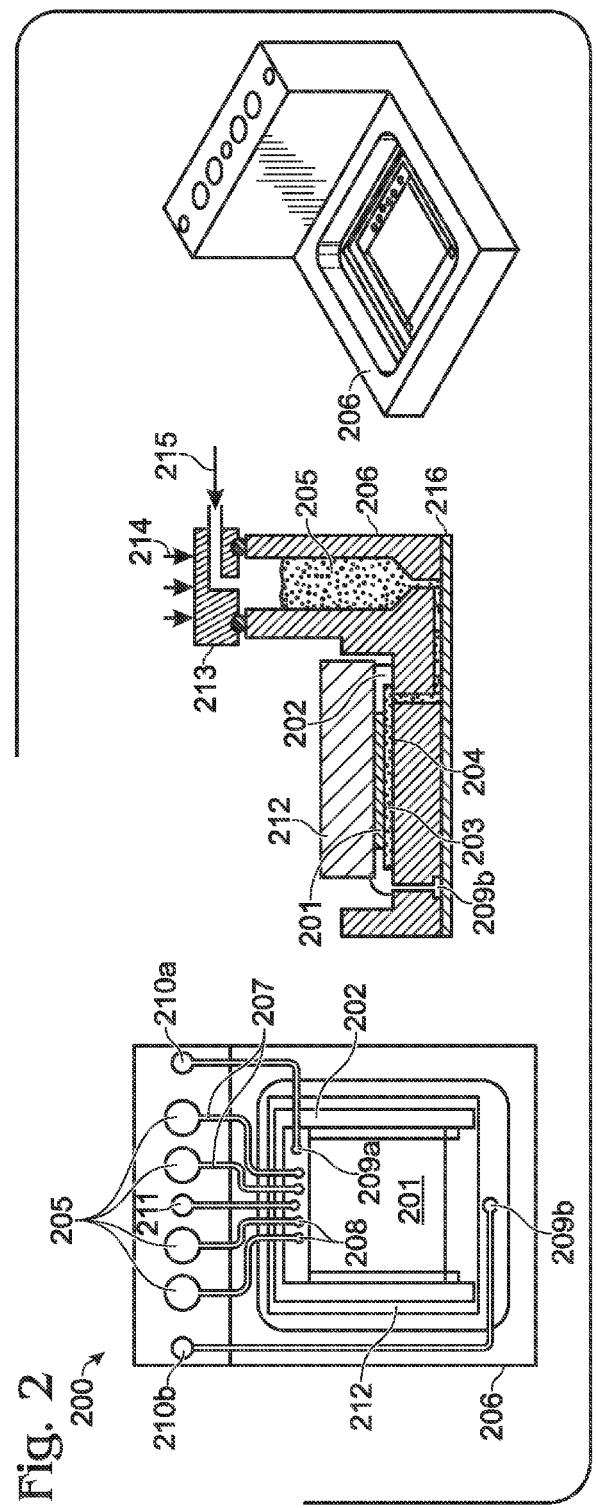

MICROFLUIDIC DEVICES FOR AUTOMATED ASSAYS

CROSS-REFERENCES TO RELATED APPLICATIONS

The present application claims priority to U.S. Provisional Application No. 61/981,617, entitled "MICROFLUIDIC DEVICES FOR AUTOMATED ASSAYS" and filed Apr. 18, 2014, the entire contents of which are incorporated herein by reference for all purposes.

BACKGROUND OF THE INVENTION

Manual methods for carrying out biological assays are time-consuming and prone to user error and contamination, problems that are exacerbated when the number of samples to be assayed increases. The pipettors and tubes that are conveniently employed in manual methods are relatively large, and thus require large amounts of sample and reagents.

Automated systems have been developed to address at least some of these problems. Conventional automated assay systems typically rely on complicated mechanics, such as XYZ-plane robots or pipettors, and/or moving stages. These systems require additional user training and represent a large investment. In addition, automated systems are often more reagent intensive, and thus more costly on a per-batch basis, than manual methods.

BRIEF SUMMARY OF THE INVENTION

The presently disclosed devices allow for automation of bioassays such as immunoassays and nucleic acid hybridization assays, and provide a very small volume for the assay. This reduces the amount of reagents and sample needed, and allows for efficient processing. The devices do not rely on complicated robotics, but can be operated with a vacuum and/or liquid or pressure line. Once sample is added to the device, no further manual attention is necessary.

Provided herein is a cartridge comprising a block frame comprising a well comprising at least one outlet, at least one inlet, and a bottom surface; and a plurality of containers embedded in the cartridge (for example, in the block frame), wherein each container is connected to the well via a microchannel (reservoir) leading to the at least one inlet.

In some embodiments, the cartridge further comprises a spacer disposed on the bottom surface of the well such that, when an assay surface (e.g., coverslip or slide) is placed on the spacer, a gap is formed between the assay surface and the bottom surface of the well. In some embodiments, the cartridge further includes an openable cover, which cover when closed is configured to enclose an assay surface and form a gap between (i) the assay surface and the bottom surface of the well or (ii) the assay surface and the cover.

In some embodiments, at least one or all of the containers are embedded in the block frame. In some embodiments, at least one or all of the containers are embedded in the cover. In some embodiments, the containers are disposed to one side of the well.

In some embodiments, the gap is formed by a spacer, wherein the spacer extends from the bottom surface of the well, and is configured to meet the cover or assay surface on the outer edge of the cover or assay surface; hold the cover or assay surface parallel to the bottom surface of the well; and leave an opening between the cover or assay surface and the bottom surface of the well through which liquid can pass (e.g., on one side of the gap). In some embodiments, the gap is formed by a spacer, wherein the spacer extends from the outer edge of the cover, and is configured to meet the bottom surface of the well and leave an opening between the cover and bottom surface through which liquid can pass when the cover is closed (e.g., on one side of the gap). In some embodiments, the spacer is sized to accommodate assay surfaces of multiple sizes (e.g., standard coverslip dimensions). In some embodiments, the assay surface, when present, is placed on the bottom surface of the well facing up, e.g., inside the border formed by the spacer. In some embodiments, the gap holds a volume of less than 500 microliters, e.g., less than 100 microliters, 10-500, 25-250, 30-100, or about 20, 30, or 50 microliters.

In some embodiments, at least one outlet leads from the bottom surface of the well. In some embodiments, at least one outlet is configured to connect (be attached) to a vacuum line. In some embodiments, the at least one inlet leads to the bottom surface of the well. In some embodiments, the outlet and at least one inlet are on opposite sides of the gap on the bottom surface of the well. In some embodiments, each container connects to a separate inlet in the well, for example in the bottom surface of the well. Each container can be connected to the well via a microchannel. In some embodiments, each container connects to a separate microchannel, wherein the microchannels merge to form a smaller number of inlets than containers.

In some embodiments, each container holds a reagent (e.g., antibody or antigen-binding fragment thereof, binding agent, probe, labeling agent, enzyme, etc.) or buffer (e.g., wash, blocking, or fixative buffer). In some embodiments, the cartridge includes an additional microchannel to allow reagent(s) and/or buffer(s) to be channeled to the well from outside the cartridge, e.g., from containers stored in an automated instrument. In some embodiments, the cartridge is attached to a manifold, through which liquid or pressure can be channeled from the automated instrument to the cartridge. In some embodiments, the manifold forms a seal with the cartridge or the plurality of containers. The contents of a container in the cartridge can be dispensed upon application of pressure to the container. In some embodiments, each of the plurality of containers is configured to be connected to a pressure or liquid line. In some embodiments, each container is attached to a valve-operated inlet channel that leads into the container. In some embodiments, the valve is in the manifold, or in the automated instrument. In some embodiments, the valve is in the cartridge.

In some embodiments, the cartridge is disposable. In some embodiments, the cartridge is packaged and stored with reagents in the containers. The cartridge can be stored at appropriate temperature if the reagents are degradable, e.g., −20° C., 0° C., or 4° C. In some embodiments, the user adds reagents to the containers before carrying out the desired assay.

In some embodiments, the cartridge is made of plastic, glass, ceramic, rubber, or non-reactive metal. In some embodiments, the cartridge is made of a polymer, e.g., a thermoplastic or elastomer, e.g., polydimethylsiloxane (PDMS), polymethyl methacrylate (PMMA), cyclic olefin copolymer (COC), cyclic olefin polymer (COP), polycarbonate (PC), or a composite thereof. In some embodiments, the block frame of the cartridge is composed of a polymer, silicon, metal, glass, or ceramic.

In some embodiments, an assay surface is included in the cartridge or loaded into the cartridge. In some embodiments the assay surface is coated on the side facing the gap. The assay surface can be coated with a known analyte or with sample. The analyte or sample can be attached directly or linked indirectly to the assay surface, e.g., via a reactive group or linker. For example, the assay surface can be coated with antibody (or antigen-binding fragment thereof), antigen, binding agent (e.g., a receptor or its ligand), protein (including glycoproteins, phosphoproteins, etc.), nucleic acid (including methylated nucleic acids, aptamers, etc.), virus or phage, cells, or cellular components (e.g., membrane fragments).

In some embodiments, the assay surface is on a coverslip or slide, e.g., made of glass or plastic. In some embodiments, the assay surface is square, rectangular, or round. In some embodiments, the assay surface is about 80-2500 square millimeters (e.g., about 100, 250, 250-1000, 300-650, or 1500-2000, mm$^2$).

In some embodiments, the cartridge further includes an additional well or trough adjacent to but separated from the well (assay area) that is configured to hold liquid. In some embodiments, the trough surrounds the well on two or three sides, and holds liquid to maintain humidity in the cartridge. In some embodiments, the cartridge further comprises a thermal element underlying the bottom surface of the well. In some embodiments, the thermal element comprises a Peltier unit, a heat sink, or both. In some embodiments, the temperature in the cartridge (and the gap) is controlled by the automated instrument.

Further provided are methods for carrying out an assay utilizing a cartridge as described herein. In some embodiments, at least one step of the assay method is automated. In some embodiments, the assay method is automated by an instrument that provides pressure, liquid, and/or vacuum lines to the cartridge.

In some embodiments, the method comprises:

placing an assay surface in a cartridge (e.g., to form a gap between the assay surface and bottom surface of the well or between the assay surface and the cover);

dispensing a first reagent from one of the plurality of containers to the well such that the first reagent enters the gap between the assay surface and the bottom surface of the well or between the assay surface and the cover;

dispensing a buffer (e.g., a wash fluid, fixative, or blocking buffer) from one of the plurality of containers or from a liquid line to the well such that the buffer displaces the first reagent in the gap;

optionally dispensing a second reagent from one of the plurality of containers to the well such that the second reagent enters the gap between the assay surface and the bottom surface of the well or between the assay surface and the cover; and optionally a dispensing buffer (e.g., a wash fluid, fixative, or blocking buffer) from one of the plurality of containers or from a liquid line to the well such that the buffer displaces the second reagent from the gap.

In some embodiments, the method further includes more than one "dispensing buffer" step between the dispensing reagents, e.g., to ensure complete washing, or to wash followed by blocking, etc. In some embodiments, the method further includes at least an additional one, two, three, or more rounds of dispensing reagent and dispensing buffer.

In some embodiments, the method further includes removing the assay surface from the cartridge after the final dispensing step (e.g., after a final wash or a fixation step) and detecting a result of the assay. In some embodiments, the method further includes detecting a result of the assay while the assay surface is in the cartridge. In some embodiments, the assay is an immunoassay. In this case, the first and second reagents can include, e.g., primary antibody and secondary antibody. In some embodiments, the assay is a nucleic acid hybridization assay. In this case, the first and second reagents can include a probe (e.g., labeled with streptavidin), and a detection agent (e.g., biotin-fluorophore).

In some embodiments, the first and second reagents and/or buffer are displaced through an opening between the assay surface and the cover, or assay surface and the bottom surface of the well (e.g., on one side of the gap). In some embodiments, dispensing comprises applying pressure to the container from which the reagent or buffer is dispensed. In some embodiments, the method further includes applying a vacuum from the outlet between or subsequent to each dispensing step. In some embodiments, in at least one step, buffer is dispensed from outside the cartridge through a microchannel in the cartridge to the well.

BRIEF DESCRIPTION OF THE DRAWINGS

FIG. 1 outlines a conventional manual assay step, with a sample 101 on a coverslip 102 placed in a petri dish or well 103. Reagent 104 (e.g., antibodies, probes, label, etc.) or buffer (e.g., wash buffer, blocking buffer, fixing agent) is pipetted into the dish or well to immerse the sample, and removed by pipette 105.

FIG. 2 shows three views of assay cartridge 200 according to embodiments of the present invention. A coverslip 201 is placed on a spacer 202 ("sealing") with sample/reagent on the bottom face. The assay is carried out in the gap 203 created between the coverslip and the bottom surface 204 of a well in the cartridge. The diagram on the left is a top view showing reagent containers 205 embedded in block frame 206, microchannels 207 leading from the reagent containers to inlets 208 on one side of the assay surface, and outlets 209a, 209b leading away from the assay surface. The outlets lead to drains 210a, 210b in the block frame. Outlet 209b occurs on the opposite side of the gap from the inlets and serves as a vent. This view also shows a "washing" microchannel 211 entering from outside the cartridge to supply wash buffer (e.g., stored in an automated instrument). The middle diagram shows that the coverslip can be held in place with a cover 212, and further shows a manifold 213 covering the reagent containers. The manifold can be secured to the block frame using a clamp 214 or other mechanism, and seal the tops of the reagent containers. A pressure line 215 directed into the manifold can be used to individually drive release of reagent or buffer from the containers into the assay gap. The bottom surface of the block frame is coated with sealing film 216. The right-most view is a simplified view of block frame 206 without the spacer, coverslip, manifold, or cover.

DETAILED DESCRIPTION OF THE INVENTION

A. Overview

Figure 3:
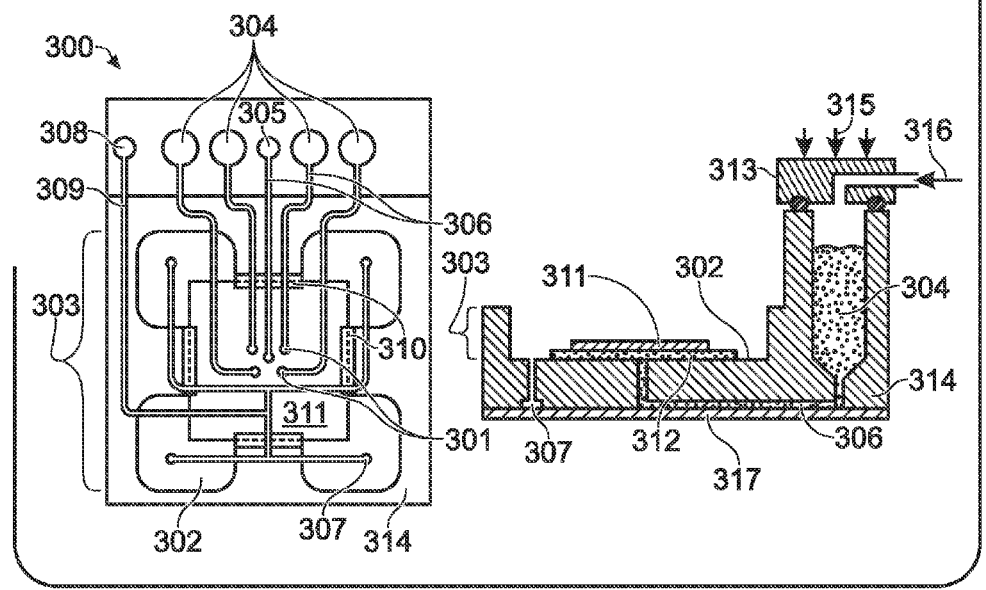
FIG. 3 shows top (left) and side (right) views of microfluidic cartridge 300 according to embodiments of the present invention. Inlets 301 are disposed in the middle of the bottom surface 302 of well 303. The inlets are connected to liquid containers 304, or to an external source of wash buffer 305, by microchannels 306. Outlets or vents 307 occur in the corners of bottom surface 302 and are connected to drain 308 by a common microchannel 309. Ledges 310 extend from the walls of well 303 and serve as sites on which the edges of coverslip 311, or another object bearing an assay surface, can rest. With the coverslip so placed, the assay surface faces downward and a small gap 312 occurs between coverslip 311 and bottom surface 302. Manifold 313 is coupled to block frame 314 by clamp 315 and seals the tops of liquid containers 304. A pressure line 316 enters the manifold and is used to drive liquids out of the containers toward inlets 301. The bottom surface of the block frame is coated with sealing film 317.

Provided herein are microfluidic cartridges for carrying out small volume biological assays. The presently described cartridges can be used for any type of assay that involves liquid processing steps and an immobilized substrate. A sample or reagent is provided on an assay surface (e.g., coverslip or slide), and assay reagents and buffers are moved across the assay surface using pressure and/or vacuum. The reagents and buffers fill a small space (gap), the height of which is determined by a spacer. The volume of the assay gap is small to minimize the amount of liquid needed, e.g., on the order of 5-500 microliters.

The cartridges can be placed in an automated instrument designed to provide pressure, liquid, and/or vacuum lines. A manifold can be clamped onto the cartridge to provide pressure and liquid lines to the containers, or to a microchannel in the cartridge that leads directly to the assay area.

The cartridge itself can include containers for reagents and/or buffers, or the reagents and/or buffers can be stored on the automated instrument. In some embodiments, small volume reagents (e.g., antibodies, affinity reagents, enzymes, detection agents) are stored in the containers in the cartridge, while buffers and wash fluids are stored in the instrument.

Reagents and buffers are channeled to the assay area in the well through microchannels (reservoirs) in the cartridge. After each step of the assay, reagents or buffers not bound to the assay surface are removed from the assay gap to a drain by vacuum and/or liquid or pressure displacement.

The gap is small in volume, and may be subject to drying. In some embodiments, a humidity control is included in the cartridge, which can include a liquid container adjacent to but separated from the well, e.g., a trough surrounding the well. In some cases, assay protocols call for different temperatures for incubation or washing. Accordingly, the cartridge can include a thermal element, e.g., underlying the bottom surface of the well, so that the temperature of the assay gap can be controlled, e.g., independently or by the larger processing instrument.

Once a user places the assay surface in the cartridge, no further manipulation is required until the assay steps are completed. Multiple cartridges can be processed together in batches, or processed under individualized conditions, depending on the needs of the user. In some embodiments, the instrument includes a detection element such as a luminometer or fluorometer, e.g., to detect label or an assay result while the assay surface is in the cartridge. In some embodiments, the cartridge and assay surface are removed from the instrument once the liquid processing steps are completed.

B. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Springs Harbor Press (Cold Springs Harbor, N.Y. 1989). Methods, devices and materials similar or equivalent to those described herein can be used in the practice of this invention. The following definitions are provided to facilitate understanding of certain terms used frequently herein and are not meant to limit the scope of the present disclosure.

The term "assay surface" refers to a substantially flat surface upon which sample or reagent is disposed. A typical assay surface is on a coverslip or slide.

Unless otherwise stated, the term "gap" refers to the volume defined by the parallel faces of an assay surface (e.g., on a coverslip or slide) placed in a well and the bottom surface of the well, or the parallel faces of the assay surface and a cover. The height of the gap is determined by the height of a spacer (sealing) between the assay surface and the bottom surface of the well or between the assay surface and the cover.

An "openable" cover refers to a cover that is attached to the cartridge, e.g., by a hinge, such that the well can be accessed, or to a cover that can be entirely removed from the cartridge.

The term "automated" refers to a device, action, or method carried out by a machine or computer without direct human control. In an automated instrument or method as described herein, at least one step is carried out automatically. The presently described cartridges can be used in a variety of assays having subjective start and end points, thus the term does not imply that all steps of an assay are carried out automatically.

The term "reagent" is used broadly to include assay components, including enzymes, antibodies, probes, binding agents (e.g., receptor or target), samples, wash fluids, buffers, detection agents, etc. Typically, however, the term is not used to refer to buffers, but to smaller volume components.

A "thermal element" refers to a heating and/or cooling element. The thermal element can be metal, ceramic, or composite. The thermal element can include, e.g., a Peltier device, a heat sink, or can be liquid-based, e.g., with liquid of a desired temperature flowing into the cartridge from the instrument.

The term "solid support" is used herein to denote a solid inert surface or body to which an agent, such as an antibody, protein, antigen, cell, or nucleic acid, can be immobilized. Non-limiting examples include glass, plastic, nitrocellulose, chips, and particles. The term "immobilized" as used herein denotes a molecular-based coupling that is not significantly de-coupled under the conditions imposed during the steps of the assays described herein. Such immobilization can be achieved through a covalent bond, an ionic bond, an affinity-type bond, or any other chemical bond.

The term "biological sample" encompasses a variety of sample types obtained from an organism. The term encompasses bodily fluids such as blood, blood components, saliva, serum, plasma, urine and other liquid samples of biological origin, solid tissue biopsy, tissue cultures, or supernatant taken from cultured cells. The biological sample can be processed prior to assay, e.g., to remove cells or cellular debris. The term encompasses samples that have been manipulated after their procurement, such as by treatment with reagents, solubilization, sedimentation, or enrichment for certain components.

The term "antibody" as used herein refers to a polypeptide encoded by an immunoglobulin gene or immunoglobulin genes, or fragments thereof, which specifically bind and recognize an analyte (antigen). The recognized immunoglobulin light chains are classified as either kappa or lambda. Immunoglobulin heavy chains are classified as gamma, mu, alpha, delta, or epsilon, which in turn define the immunoglobulin classes, IgG, IgM, IgA, IgD and IgE, respectively.

An example of a structural unit of immunoglobulin G (IgG antibody) is a tetramer. Each such tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively.

Antibodies exist as intact immunoglobulins or as well-characterized fragments produced by digestion of intact immunoglobulins with various peptidases. Thus, for example, pepsin digests an antibody near the disulfide linkages in the hinge region to produce F(ab')2, a dimer of Fab which itself is a light chain joined to VH-CH1 by a disulfide bond. The F(ab')2 dimer can be reduced under mild conditions to break the disulfide linkage in the hinge region, thereby converting the F(ab')2 dimer into two Fab' monomers. The Fab' monomer is essentially an Fab with part of the hinge region (see, Paul (Ed.), *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or by de novo synthesis using recombinant DNA methodologies such as single chain Fv.

The terms "antigen," "immunogen," "antibody target," "target analyte," and like terms are used herein to refer to a molecule, compound, or complex that is recognized by an antibody, i.e., can be specifically bound by the antibody. The term can refer to any molecule that can be specifically recognized by an antibody, e.g., a polypeptide, polynucleotide, carbohydrate, lipid, chemical moiety, or combinations thereof (e.g., phosphorylated or glycosylated polypeptides, etc.). One of skill will understand that the term does not indicate that the molecule is immunogenic in every context, but simply indicates that it can be targeted by an antibody.

Antibodies bind to an "epitope" on an antigen. The epitope is the localized site on the antigen that is recognized and bound by the antibody. Epitopes can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The terms "specific for," "specifically binds," and like terms refer to a molecule (e.g., antibody or antibody fragment) that binds to its target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a given antibody target will typically bind the antibody target with at least a 2-fold greater affinity than a non-antibody target. Specificity can be determined using standard methods, e.g., solid-phase ELISA immunoassays (see, e.g., Harlow & Lane, *Using Antibodies, A Laboratory Manual* (1998) for a description of immunoassay formats and conditions that can be used to determine specific immunoreactivity).

The term "nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The term "aptamer" refers to short nucleic acid sequences (usually 20-200 bases in length) that bind to a targeted molecule via non-Watson-Crick interactions with high affinity. Aptamers can include modified nucleic acids. The design and selection of target-specific aptamers is known in the art, e.g., as described in U.S. Pat. Nos. 5,270,163, 5,567,588, and 5,475,096, and Klug and Famulok (1994) *Mol. Biol. Reports* 20:97-107.

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs are compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics are chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are often considered conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The terms "identical" or "percent identity," in the context of two or more nucleic acids, or two or more polypeptides, refer to two or more sequences or subsequences that are the same or have a specified percentage of nucleotides, or amino acids, that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical."Percent identity can be determined over optimally aligned sequences, so that the definition applies to sequences that have deletions and/or additions, as well as those that have substitutions. The algorithms commonly used in the art account for gaps and the like. Typically, identity exists over a region comprising an antibody epitope, or a sequence that is at least about 25 amino acids or nucleotides in length, or over a region that is 50-100 amino acids or nucleotides in length, or over the entire length of the reference sequence.

The term "binds" with respect to an affinity agent and binding target (e.g., antibody-antigen, receptor-receptor target, complementary nucleic acids), indicates that an agent binds a majority of the targets in a pure population (assuming appropriate molar ratios). For example, an agent that binds a given target typically binds to at least ⅔ of the targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

The specificity of the binding can be defined in terms of the comparative dissociation constants (Kd) of the targeting agent for target, as compared to the dissociation constant with respect to the targeting agent and other materials in the environment or unrelated molecules in general. In some embodiments, the Kd of the targeting agent with respect to the unrelated material will be at least 2-fold, 3-fold, 4-fold, 5-fold, 10-fold, 20-fold, 50-fold, 100-fold, 200-fold or higher than Kd with respect to the target.

A targeting moiety can bind with a Kd of less than about 1000 nM, e.g., less than 250, 100, 50, 20 or lower nM. In some embodiments, the Kd of the affinity agent is less than 15, 10, 5, or 1 nM. In some embodiments, the Kd is 1-100 nM, 0.1-50 nM, 0.1-10 nM, or 1-20 nM. The value of the dissociation constant (Kd) can be determined by well-known methods, and can be computed even for complex mixtures by methods as disclosed, e.g., in Caceci et al., Byte (1984) 9:340-362.

Affinity of a targeting agent for a target can be determined according to methods known in the art, e.g., as described herein and reviewed in Ernst et al. Determination of Equilibrium Dissociation Constants, *Therapeutic Monoclonal Antibodies* (Wiley & Sons ed. 2009). A modified ELISA format can also be used (see Lequin (2005) *Clin. Chem.* 51:2415-18 for a review of several ELISA formats).

The terms "label," "detectable label, "detectable moiety," and like terms refer to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, digoxigenin, $^{32}P$ and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating label to a desired agent may be employed, e.g., using methods described in Hermanson, *Bioconjugate Techniques* 1996, Academic Press, Inc., San Diego.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters, and will understand which controls are valuable in a given situation and be able to analyze data based on comparisons to control values. Controls are also valuable for determining the significance of data. For example, if values for a given parameter are variable in controls, variation in test samples will not be considered as significant.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

C. Cartridge and Assay Surface Materials

The matrix that forms the cartridge or solid support (assay surface) can be any material that is compatible with the presently described assays. The matrix should be inert to the components of the biological sample and to the assay reagents, and be solid and insoluble in the sample and in any other reagents or washes used in the assay.

Examples of suitable materials are polymers such as plastics, polyesters, polyethers, polyolefins, polyalkylene oxides, polyamides, polyurethanes, polysaccharides, celluloses, and polyisoprenes. Thermoplastics and elastomers can be used, e.g., polydimethylsiloxane (PDMS), polymethyl methacrylate (PMMA), cyclic olefin copolymer (COC), cyclic olefin polymer (COP), polycarbonate (PC). Crosslinking is useful in many polymers for imparting structural integrity and rigidity. Polymer-based cartridges are conveniently made by injection molding. Further examples of appropriate materials include glass, ceramic, silicon, non-reactive metals and hard rubber.

The assay surface should be capable of affixing an assay reagent (e.g., target, targeting agent, cells, proteins, antibodies, or nucleic acids). Assay reagents often adhere to certain surfaces without modification. For example, fibroblasts and other adherent cells can be grown on plastic or glass. Functional groups for attachment of the assay reagent can be incorporated into the assay surface, if desired, by conventional means. Examples of suitable functional groups are amine groups, ammonium groups, hydroxyl groups, carboxylic acid groups, and isocyanate groups. The assay reagent can be covalently bound to the assay surface, either directly or indirectly, e.g., with a linking group. Linking groups can be used as a means of increasing the density of reactive groups on the assay surface and decreasing steric hindrance to increase the range and sensitivity of the assay, or as a means of adding specific types of reactive groups to the solid phase surface to broaden the range of types of assay reagents that can be affixed to the assay surface. Examples of suitable useful linking groups are polylysine, polyaspartic acid, polyglutamic acid and polyarginine.

The assay surface can be on a coverslip (e.g., 18 mm×18 mm, 25 mm×25 mm, or round, e.g. with a radius of 10-50 mm) or glass slide (e.g. 25 mm×75 mm).

D. Cartridge Construction

A cartridge according to embodiments of the present invention includes a block frame. The block frame can be formed from a monolithic block of material or from pieces of material joined together. Any convenient materials, such as those disclosed above, can be used. In some embodiments, the block frame is rigid and resists mechanical deformation. In some embodiments, the block frame is formed from or coated with chemically inert materials, and is not susceptible to chemical degradation from exposure to biological samples, acids, bases, aqueous solutions, organic solutions, buffers, or reagents with which it may come into contact. Exterior surfaces of the block frame can be covered with sealing film to seal open ports or channels from the outside space. The sealing film can be removed at a desired time to make these ports or channels accessible to pressure or liquid sources, for example.

The block frame includes one or more wells, each of which can be a depression or indentation in the frame. A well includes a bottom surface, which can be substantially flat or planar, and optionally one or more walls adjacent to and extending upward from the bottom surface (see, for example, FIG. 2, right panel). The well also includes at least one inlet and at least one outlet, which can be used to exchange fluids (i.e., liquids and gases) between the well and spaces outside the well. For example, an inlet can be used to introduce buffers or reagents into the well or into a gap formed inside the well. An outlet can be used to drain liquids from the well or vent gases displaced by liquids introduced into the well. Positive or negative pressure can also be applied through an inlet or outlet, for example in the form of an air stream or vacuum. Each inlet or outlet includes a hole or aperture in the block frame that opens into the well. The hole can be located in the bottom surface of the well or a wall adjacent to the bottom surface, for example. The hole can be connected to a microchannel or other passage leading away from the well, for example to a liquid container.

Inlets and outlets can be positioned in the well as desired. In some embodiments, multiple inlets are clustered together on the bottom surface of the well, for example within at most 0.1, 0.2, 0.5, 1, 2, or 5 $cm^2$ of this bottom surface. At least 2, 3, 4, 5, 10, 20, 50, or 100 inlets can be so clustered. In some embodiments, one or more inlets occur at the edge of the bottom surface of the well, for example at most about 0.1, 0.2, 0.5, 1, 2, 5, or 10 cm from where the bottom surface joins a wall of the well. In other embodiments, one or more inlets occur near the center of the bottom surface of the well, for example at least about 0.1, 0.2, 0.5, 1, 2, 5, or 10 cm away from where the bottom surface joins a wall of the well. Similarly, one or more outlets can be located at the edge of the bottom surface of the well or near the center. In some embodiments, an outlet is coupled to a microchannel that is directed downward from the bottom surface of the well. This microchannel can connect to a drain in the block frame and/or a vacuum source, and can lead to the space below the block fame.

The well can accommodate an assay surface on which a reagent, biological sample, or components thereof can be disposed. The assay surface can be on a microscope coverslip, plastic slide, or other object dimensioned to lie flat on the bottom surface of the well, and/or lie parallel to this surface, so that at least one side of the object can be exposed to liquids in the well. The object bearing the assay surface can be mechanically secured inside the well, for example using screws or an adhesive, or can rest on the bottom surface of the well or another object. In some embodiments, this object is positioned along the bottom surface of the well so that it lies between the inlets and outlets, and does not overlap them.

In some embodiments, a spacer is placed inside the well along with the assay surface. The spacer can be made of rubber, plastic, foam, or another convenient material, and if desired can be affixed to or embedded in the bottom surface of the well. The spacer can also be affixed to the assay surface, for example as a rubber gasket running around the perimeter of a microscope coverslip or plastic slide. The spacer is used to mediate the height of a gap formed between the assay surface and another surface in the well, and thereby mediate the depth of fluid to which the assay surface is exposed. In some embodiments, the spacer is mechanically deformable but can be used to establish a gap of consistent height. In some embodiments, the spacer forms a liquid- or gas-tight seal with another object that it contacts. The other object can be the assay surface or the bottom surface of the well, for example. The spacer can alternatively be called a "seal" or "sealing."

In some embodiments, the cartridge also includes a cover. The cover can fit inside and/or cover a well formed in the block frame, thereby preventing contaminants from outside the well from contacting liquids in the well or the assay surface. The cover can be opened to expose the well. In some embodiments, the cover is attached to the block frame with a hinge or other mechanism, or simply rests in place on the block frame by friction.

Figure 4:
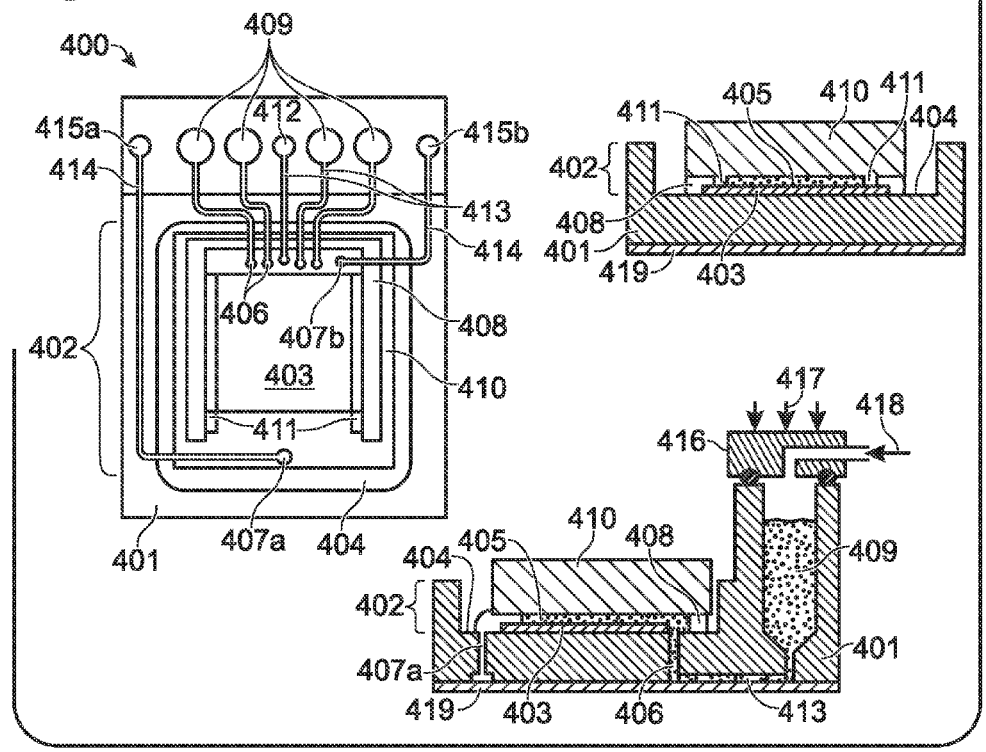
FIG. 4 shows three views of assay cartridge 400 according to embodiments of the present invention. On the left is a top view, at bottom is a side view, and in the upper-right is a face-on side view. Block frame 401 includes a well 402. Coverslip 403 is placed on the bottom surface 404 of the well, so that the assay surface faces up. An assay gap 405 is formed between coverslip 403 and cover 410. Inlets 406 and outlet 407a occur in bottom surface 404 and on opposite sides of gap 405. A line connecting the inlets 406 and outlet 407a defines a direction of flow in the cartridge, going from top to bottom in the top view of the cartridge (left panel) and from right to left in the side view (bottom panel). Pieces of spacer 408 are placed on the bottom surface of the well adjacent to coverslip 403 and extend parallel to the direction of flow. In addition, a piece of spacer is positioned near the wall of the well closest to liquid containers 409. The spacer can contact cover 410 when the coer is lowered into the well, so that the cover rests on the spacer. In addition, protrusions 411 in cover 410 extend downward from the bottom surface of the cover and run parallel to the direction of flow. The protrusions can contact coverslip 403 at its periphery when the cover is lowered. Together, spacer 408 and protrusions 411 prevent the bottom surface of cover 410 from contacting coverslip 403 over its full area, and allow gap 405 to be established. Inlets 406 are connected to liquid containers 409, or to an external source of wash buffer 412, through microchannels 413. Similarly, microchannels 414 lead from outlets 407a and 407b to drains 415a and 415b, respectively, in block frame 401. Manifold 416 is coupled to the block frame with clamp 417 and is connected to external pressure source 418. The bottom surface of block frame 401 is covered with sealing film 419.

The cover can also be used to form a gap inside the well adjacent to the assay surface. In some embodiments, the spacer extends from the bottom surface of the well, upward toward the cover. If the object bearing the assay surface is also disposed on the bottom surface of the well (for example, with one or more pieces of spacer surrounding it), then the spacer can contact the cover (for example, at the outer edges of the cover) when the cover is lowered (FIG. 4). The spacer thus leaves a gap between the cover and the assay surface. In this configuration, the assay surface is exposed to the gap and faces upward. In some embodiments, the spacer is positioned to leave an opening between the cover and the assay surface through which liquid can pass, for example on one side of the gap. This opening can occur on the edge of the assay surface nearest the outlet, so that liquid can pass out of the gap between cover and the assay surface and toward the outlet. In some embodiments, openings occur on both sides of the gap, such that an unobstructed fluidic pathway runs between the inlet(s) and outlet(s) and through the gap. In these embodiments, the spacer can include two strips of material running parallel to such a pathway.

Alternatively, the object bearing the assay surface can rest on top of the spacer (for example, the edges of a microscope coverslip can contact the spacer), such that a gap occurs between the assay surface and the bottom surface of the well (FIG. 2). When the cover is lowered, it can press the object against the spacer, thereby mediating the height of the gap, or restrict the movement of the object in the well. Another alternative is for the object to be affixed directly to the cover, such that the assay surface and/or the cover contacts the spacer when the cover is lowered, and a gap is formed between the assay surface and the bottom surface of the well. In these configurations, the assay surface faces downward, and openings through which liquid can pass can occur (as above) on one or both sides of the gap.

In other embodiments, the spacer extends from the cover downward and is configured to meet the bottom surface of the well when the cover is lowered. In some embodiments, the spacer extends from an outer edge of the cover, for example around the periphery of the cover. Upon lowering the cover over the well, a gap is formed between the cover and the bottom surface of the well. In these embodiments, an object bearing the assay surface can be placed inside the spacer, for example in the middle of the well. This object can be adjacent to the cover, in which case the assay surface faces downward, or adjacent to the bottom surface of the well, in which case the assay surface faces upward. The spacer can be shaped or positioned as desired to leave an opening between the cover and the bottom surface of the well, through which liquid can pass, when the cover is closed. Such an opening can occur on one or both sides of the gap.

If desired, the object bearing the assay surface can be thinner than the spacer in a direction perpendicular to the bottom surface of the well. The spacer can be generally configured so that a portion of the gap is open to the space outside the cartridge, and liquid or gas is not prevented from exiting the gap by the spacer. In any embodiment, the gap between the assay surface and the bottom surface of the well, or between the assay surface and the cover, can be at least about 1, 2, 5, 10, 20, 50, 100, 200, 500, or 1000 microns in height.

The configurations of the block frame, well, assay surface, spacer, and cover can be varied as desired. Some variations are illustrated in FIGS. 2-8. In some embodiments, the well contains a ledge on which the cover can rest, wherein the ledge is elevated above the bottom surface of the well. Alternatively or in addition, the cover can include downward-facing protrusions to contact the bottom surface of the well, or the edges of the assay surface, when the cover is closed. Along with one or more spacers, the ledge or protrusions can facilitate the formation of a gap of desired height adjacent to the assay surface.

Figure 7:
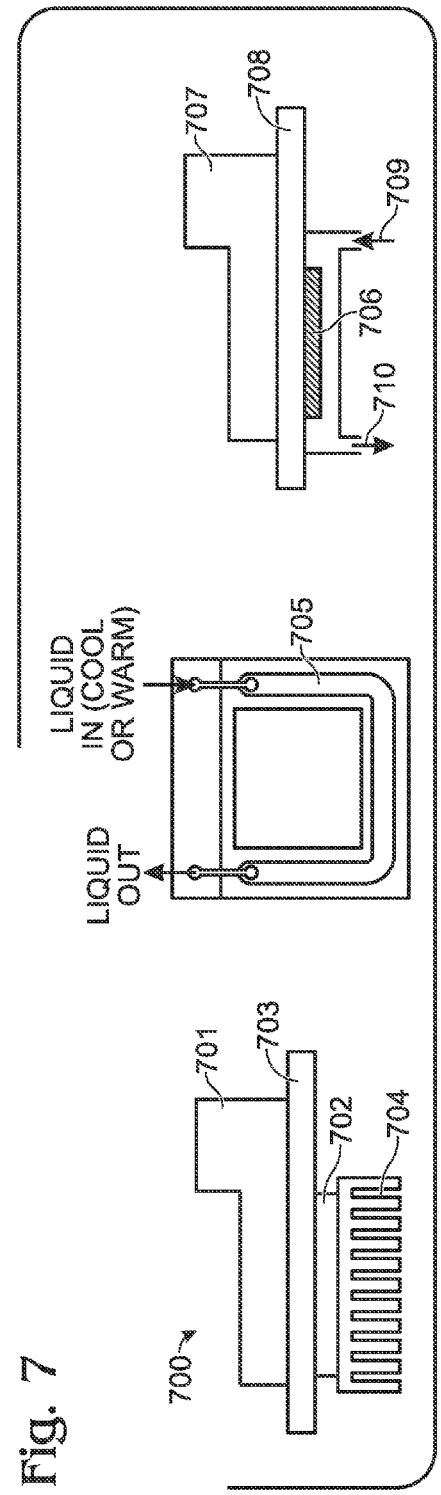
FIG. 7 shows cartridges according to embodiments of the present invention, wherein the cartridge includes a thermal unit disposed below the assay area. The temperature for each cartridge in a device can be independently controlled, e.g., depending on the assay step or required conditions. In the left side view, cartridge 700 includes block frame 701 coupled to Peltier unit 702 through solid substrate 703. Heat sink 704 is disposed below the Peltier unit. In the center view, the temperature of the assay area is modulated with a liquid (cool or warm), which circulates around the assay area, for example in trough 705, such that heat can be exchanged between the liquid and assay area. At right, heater 706 is coupled to block frame 707 through solid substrate 708, and a fluid (liquid or gas) is passed over the heater, from entrance port 709 to exit port 710. The fluid, upon passing through the entrance port, can be of a different temperature from the heater, and can thus exchange heat with the heater as it passes through. Thus, the fluid can mediate the amount of heat imparted to the assay area, and regulate the temperature of the assay area.
Figure 6:
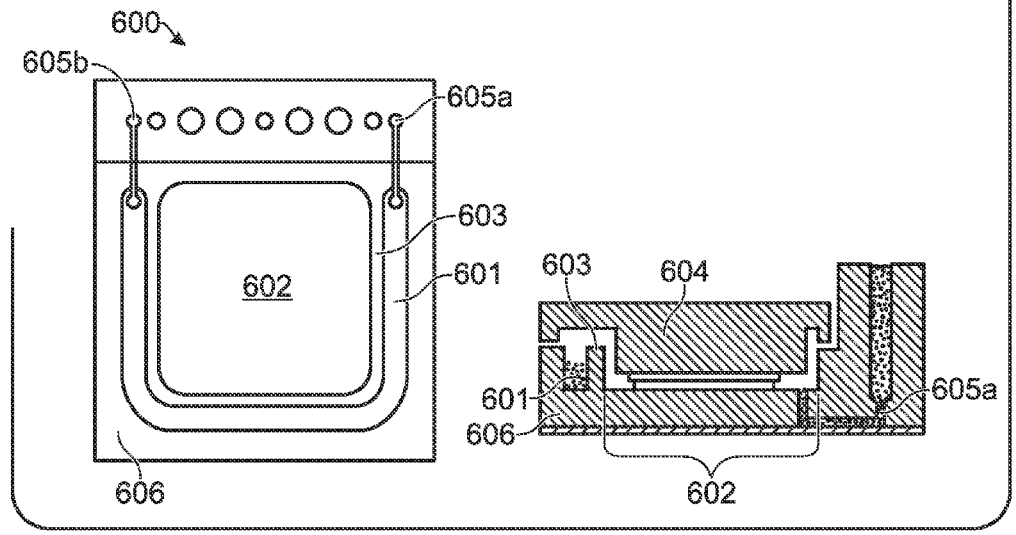
FIG. 6 shows a cartridge 600 that includes a liquid trough 601, e.g., to control humidity. The liquid in the trough is separated from assay area 602 by barrier 603, but cover 604 is configured to enclose both the trough 601 and assay area 602. In the embodiment shown, liquid enters and exits the trough through microchannels 605a and 605b, respectively, in block frame 606. The microchannels lead to the space outside the cartridge.
Figure 8:
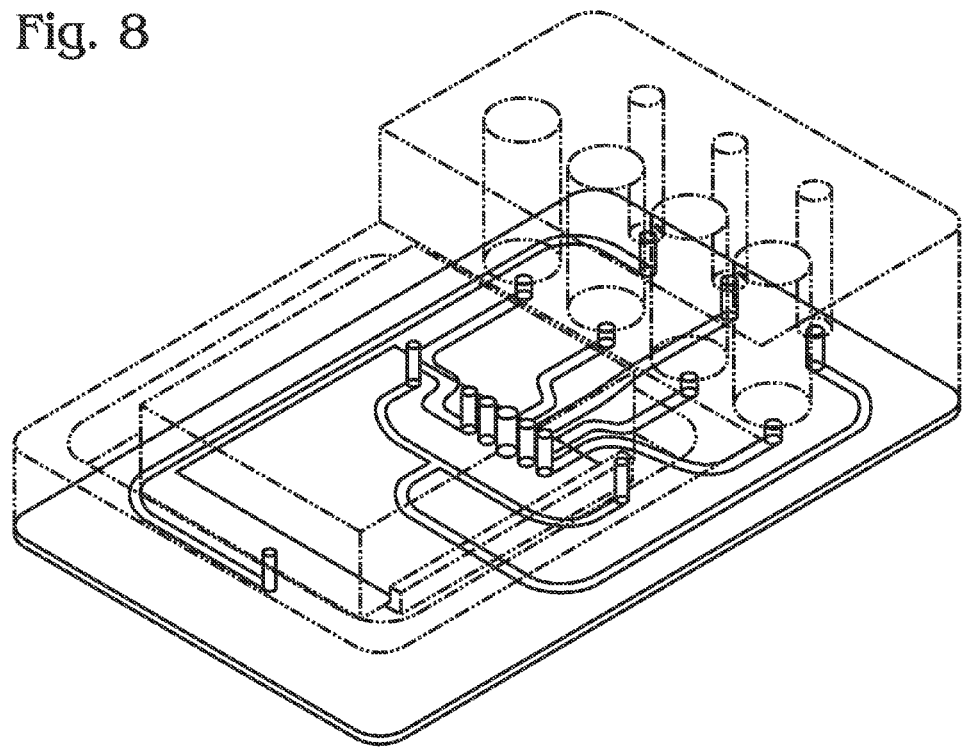
FIG. 8 is a transparent view of an embodiment of a cartridge with reagent/buffer containers connected to the assay gap by microchannels. A drain in the bottom surface is shown in the foreground, and leads to an outlet at the back of the cartridge.

In some embodiments, the cartridge further includes an additional well or a trough adjacent to but separated from the well in which the assay surface is placed (FIGS. 6 and 7). The trough can be disposed in the block frame and can be configured to maintain humidity in the cartridge. In some embodiments, the trough surrounds the assay well on two or three sides and is separated from the well by a solid barrier. The solid barrier can be shorter than the gap formed by any spacer, or taller than this gap, as desired. In some embodiments, the trough and well can be enclosed by the same openable cover, such that both the trough and well are exposed to the same air sample and humidity can be transferred between the trough and well through the air. A liquid such as water can be flowed through the trough, and if desired a separate inlet and outlet can be connected to the trough to regulate the amount of liquid present.

In some embodiments, the bottom surface of the well is sloped or angled to facilitate the flow of liquid in a desired direction, for example from an inlet to an outlet. Thus, a gap formed between the bottom surface and an assay surface can have non-uniform depth. In some embodiments, an inlet is located at a site on the bottom surface of the well that is higher than the site for an outlet, so that liquid can flow downhill from the inlet to the outlet. In some embodiments, an outlet occurring at a low point in the bottom surface of the well serves as or connects to a drain. Flow can also be regulated by open grooves or channels cut into the bottom surface of the well, or obstacles to flow (such as bumps or ridges) protruding from the bottom surface. In some embodiments, the bottom surface of the well is passivated, for example, with a non-stick or hydrophobic coating, to prevent liquids, reagents, or contaminants from adhering to the surface while the cartridge is being used in an assay or is in storage.

A cartridge as provided herein also includes a plurality of containers embedded in the block frame. The containers are configured to store liquids, and deliver liquid to the well through the inlets. In some embodiments, each container is connected to the well via a microchannel leading to at least one inlet.

Any desired number of liquid containers can be embedded in the block frame—for example, at least 2, 3, 4, 5, 6, 7, 8, 9, 10, 15, 20, 50, or 100 containers. In some embodiments, one or more liquid containers has a long axis that is oriented vertically, and is connected at the base of the container to a microchannel leading to the well. Thus, liquid can drain from the container into the well with minimal driving force. In some embodiments, one or more containers is disposed above the bottom surface of the well, so that liquid can be siphoned from the container into the well. In some embodiments, the containers are cylindrical in shape. Each container can be coupled to one or more pumps, valves, syringes, or other mechanisms to regulate the flow of liquid out of the container. The containers can be disposed to one side of the well, as shown in FIGS. 2-4 and 8.

The liquid containers can be connected to one or more inlets in the well of the cartridge as desired. In some embodiments, each container connects to a separate inlet, for example via a microchannel. The containers can be equal in number to the inlets, and can be fluidically segregated from each other upstream of the inlets. In other embodiments, the block frame contains a branched network of microchannels leading from the liquid containers to the inlets. In these embodiments, one or more microchannels can merge upstream of the inlet, so that liquids carried in these microchannels can mix or travel over the same path before entering the well through a common inlet. The microchannels leading from 2, 3, 4, 5, or more liquid containers can thus be connected to the same inlet. Alternatively, a microchannel leading from one liquid container can be split into multiple branches, so that liquid from this container can be delivered to multiple inlets in the well. One, 2, 3, 4, 5, or more inlets can thus be fed with liquid from the same liquid container.

Microchannels in the block frame can have any desired dimensions. For example, a microchannel can have a width of at least about 1, 10, 100, 1,000, or 10,000 micrometers, or can be dimensioned to allow laminar or turbulent flow. In some embodiments, the width of a microchannel is at most about 1, 10, 100, 1,000, or 10,000 micrometers. In some embodiments, the width of a microchannel falls within the range of about 1-10, 1-100, 1-1,000, 1-10,0000, 10-10,000, 100-10,000, 1000-10,000, 10-100, or 100-1,000 micrometers. The microchannels disposed in the block frame can all have the same width or can have different widths. For example, a microchannel that is used to deliver a liquid to the well in relatively large quantities can be wide, to allow faster delivery, while another microchannel used to deliver liquids in small quantities can be narrow. Likewise, a single microchannel can vary in width along its length to regulate aspects of fluid flow such as flow rate or pressure.

Microchannels disposed in the block frame can also be coupled to valves or pumps to regulate liquid or gaseous flow. For example, a microchannel leading from a liquid container to an inlet in the well can be coupled at either end to a valve or pump (for example, at the outlet of the liquid container, or at the aperture of the inlet), or anywhere along the length of the microchannel. In some embodiments, a pump or valve coupled to a microchannel is fully contained or embedded in the block frame. The microchannels can be bored directly into the block frame, or can be carried by tubing, capillaries, or other conduits through the block frame.

In some embodiments, the cartridge also includes a manifold (see, for example, FIGS. 2-5). The manifold can be clamped or otherwise positioned on the block frame adjacent to the liquid containers, and can seal one or more containers from the space outside the cartridge. The manifold can contact the block frame using rubber gaskets, O-rings, or other appropriate sealing means. In some embodiments, the manifold is coupled to a liquid source (for example, in an instrument into which the cartridge is inserted) and is used to supply liquids to one or more containers, for later delivery to the well of the cartridge. The manifold can also be coupled to a vacuum or pressure source, and can be used to regulate the flow of liquids into or out of the containers.

In some embodiments, the manifold is coupled to a microchannel in the block frame that leads directly to the well, for example to an inlet or outlet. Thus, liquids can be delivered directly from the manifold to the well without first passing through a container in the block frame, and/or can be removed from the well to the manifold. A channel connecting a manifold or instrument to a well of the cartridge is referred to as a "liquid line," and in some embodiments is configured to accommodate buffers (e.g., wash fluids) used to displace reagents from the well. Likewise, gases can be introduced to or removed from the well via a microchannel coupled directly to the manifold.

Figure 5:
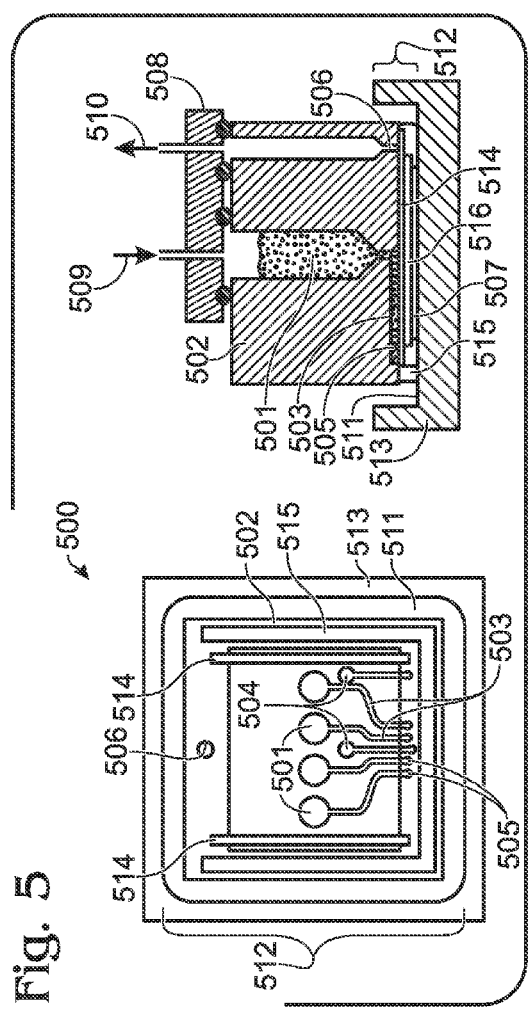
FIG. 5 shows top (left) and side (right) views of assay cartridge 500 according to embodiments of the present invention. Liquid containers 501 are embedded in cover 502 and store reagents. Microchannels 503 connect these containers and external liquid sources 504 to inlets 505 in the bottom surface of cover 502. An outlet 506 is also disposed in the bottom surface of the cover, on the opposite side of coverslip 507 from inlets 505, and provides a route for fluid drainage by vacuum. Cover 502 is sealed to manifold 508, which is turn connected to at least one pressure line 509 and vacuum line 510. Coverslip 507 is shown placed on the bottom surface 511 of a well 512 of the cartridge, with the sample side up. The well is formed in base 513. Protrusions 514 in the bottom surface of the cover, and/or spacers 515, are disposed parallel to the direction of liquid flow in the cartridge and separate the coverslip from a flat portion of the bottom surface of the cover. Thus, gap 516 occurs between the coverslip and cover.

In some embodiments, one or more liquid containers are disposed in the cover of the cartridge, as shown in FIG. 5. These containers can be used in lieu of or in addition to any containers embedded in the solid block to facilitate fluid flow in the cartridge. As desired, containers in the cover can be fluidically coupled to the well adjoining the cover. For example, a container in the cover can be connected by microchannel to an inlet or outlet in a surface of the cover. This surface, for example a bottom surface of the cover, can be exposed to a gap between the cover and an assay surface. Thus, one or more liquids for an assay can be introduced through an inlet in the cover rather than an inlet occurring in the bottom surface of the well. Liquids or gases can also be removed through an outlet in the cover. In some embodiments, a manifold is coupled to the cover to deliver liquids or pressure to one or more containers or microchannels in the cover. Instead or in addition, the manifold can be used to draw a vacuum against a container or microchannel in the cover.

In some embodiments, the cartridge includes one or more inlets in a bottom surface of the cover, and one or more outlets in a bottom surface of the well. In some embodiments, the cartridge includes one or more outlets in a bottom surface of the cover, and one or more inlets in a bottom surface of the well. In some embodiments, at least one inlet and at least one outlet are disposed in a bottom surface of the cover.

The cartridge can also include a thermal unit underlying the bottom surface of the well. The thermal unit can be used to regulate the temperature of assays performed in the cartridge. In some embodiments, the thermal unit includes a Peltier device and/or a heat sink. In some embodiments, the bottom surface of the well is thermally conductive. The thermal unit can be directly coupled to the block frame of the cartridge, for example with metal screws, plastic screws, or a thermally conductive adhesive. Alternatively, the thermal unit can be separated from the block frame by a solid substrate, which can be thermally conductive or insulating. The thermal unit can underlie the entire well or a portion thereof (for example, a region near one or more inlets, or a region near one or more outlets). The thermal unit can provide or remove heat uniformly over the full area of the bottom surface of the well, or can do so with areal variation or specificity. For example, the thermal unit can heat one part of the well while cooling another part, or provide heat to only part of the well while not directly applying heat to the rest of the well. In some embodiments, the thermal unit can be used to establish temperature gradients across the well. In cartridges containing multiple wells, a different thermal unit can be associated with each well. These thermal units can be controlled independently, and the wells can be subjected to different thermal protocols.

If desired, the thermal unit can be operated in concert with fluid flow to obtain the desired temperature profile in a well of the cartridge. For example, liquid can be flowed through a humidifying trough around the well as discussed above, wherein the liquid is maintained at a different temperature from the thermal unit (see FIG. 7, center panel). Thus, the center of the well can be heated by the thermal unit while the periphery of the well can be cooled by liquid in the trough, or vice versa. Alternatively, liquid or gas can be flowed directly past the thermal unit as shown in FIG. 7, right panel, so that the thermal unit is heated or cooled and the temperature of the well is mediated.

E. Assays

The presently disclosed cartridges can be used for any biological assay involving a sample or reagent disposed on a substantially flat assay surface, and liquid processing steps. Non-limiting examples include immunoassays, other protein-based affinity assays, and nucleic acid hybridization assays.

In some embodiments, the assay surface is coated (directly or indirectly) with antibodies or binding fragments thereof, e.g., specific for a particular cell type or known analyte. In some embodiments, the assay surface is coated with protein having a known affinity for a particular cell type or analyte, or with a heterogeneous protein sample. In some embodiments, the assay surface is coated with cells, e.g., from an in vitro culture sample, or from a patient sample. In some embodiments, the assay surface is coated (directly or indirectly) with primers or probes that will specifically hybridize to a known sequence, or with a heterogeneous nucleic acid sample.

Immunoassays that can be carried out on the presently disclosed cartridges include, for example, enzyme linked immunoabsorbent assay (ELISA), fluorescent immunosorbent assay (FIA), immunohistochemistry, chemical linked immunosorbent assay (CLIA), radioimmuno assay (RIA), competitive and non-competitive assay systems, e.g., "sandwich" immunoassays, immunoprecipitation assays, precipitin reactions, immunodiffusion assays, immunoradiometric assays, fluorescent immunoassays, etc. For a review of applicable immunoassays, see, e.g., The Immunoassay Handbook, David Wild, ed., Stockton Press, New York, 1994; Ausubel et al, eds, 1994, Current Protocols in Molecular Biology, Vol. 1, John Wiley & Sons, Inc., New York.

ELISAs include a number of variations. In some cases, the ELISA comprises preparing a sample that potentially includes an antigen, coating the coverslip or other matrix material with the sample, adding primary antibody, incubating for a period of time, washing away unbound material, adding labeled secondary antibody, incubating, and washing. One of skill in the art would be knowledgeable as to other variations of ELISAs, e.g., where target is labeled and the primary antibody is coated on the matrix material, etc.

Immunoprecipitation and immunoseparation protocols can comprise contacting a sample with primary antibody specific for the desired target in the sample, incubating for a period of time (e.g., 1-4 hours at 4° C.), optionally adding secondary antibody for detection, and incubating, washing, and recovering the target in an SDS/sample buffer or elution buffer. Again, one of skill will be familiar with variations of immunoprecipitations, e.g., using Protein A, Protein G, Protein A/G, secondary antibody, or target as the binding partner for primary antibody.

Similar methods can be employed for any affinity-based assay (e.g., protein, glycoprotein, phosphoprotein, lipid, or carbohydrate-based), or for detecting cells based on surface expression of a known target. In some embodiments, the assay involves a cell sample, e.g., cells grown on the assay surface. For example, the cells on the assay surface can be exposed to a first reagent that binds a cell surface marker, washed, exposed to a second reagent that binds a different cell surface marker, or that binds to the first reagent, washed, exposed to a third reagent that, e.g., binds the first and/or second reagent and can be detected, washed, etc. The assay surface (e.g., coverslip) can then be removed from the cartridge for detection, or detection can take place in the cartridge.

The presently disclosed cartridges can be used for nucleic acid hybridization assays, e.g., to detect expression levels, genetic variants, or single nucleic acid polymorphisms (SNPs). Methods for detection include nucleotide arrays (e.g., a homologous or heterogeneous population of nucleic acid primers or probes disposed on the assay surface), sequencing, and amplification methods, etc. Primers or probes are designed to hybridize to a target sequence. For example, genomic DNA can be screened for the presence of an identified genetic element of using a probe based upon one or more sequences, e.g., using a probe with substantial identity to a subsequence of a targeted gene. Expressed RNA can also be screened for sequence and/or quantity.

A probe can be between 10-500 nucleotides in length, e.g., 10-100, 10-40, 10-20, 20-100, 100-400, etc. In some embodiments, the sequence to be detected includes 8 contiguous nucleotides, e.g., at least 10, 15, 20, 25, 30, 35 or more contiguous nucleotides of a known sequence.

The assay can be varied for stringency, to allow binding of only 100% complementary sequences of a given length, or less than 100%. As the conditions for hybridization become more stringent, there must be a greater degree of complementarity between the probe and the target for duplex formation to occur. Thus, high stringency conditions are typically used for detecting a SNP.

The degree of stringency can be controlled by temperature, ionic strength, pH and/or the presence of a partially denaturing solvent such as formamide in the buffer. For example, the stringency of hybridization is conveniently varied by changing the concentration of formamide within the range up to and about 50%. The degree of complementarity (sequence identity) required for detectable binding will vary in accordance with the stringency of the hybridization medium and/or wash medium. In certain embodiments, in particular for detection of a particular SNP, the degree of complementarity is about 100 percent. In other embodiments, sequence variations can result in <100% complementarity, <90% complementarity probes, <80% complementarity probes, etc., in particular, in a sequence that does not involve a SNP. In some examples, e.g., detection of species homologs, primers may be compensated for by reducing the stringency of the hybridization and/or wash medium.

High stringency conditions for nucleic acid hybridization are well known in the art. For example, wash or incubation conditions may include low salt and/or high temperature, such as provided by about 0.02 M to about 0.15 M NaCl at temperatures of about 50° C. to about 70° C. The temperature and ionic strength of a desired stringency are determined in part by the length of the particular nucleic acid(s), the length and nucleotide content of the target sequence(s), the charge composition of the nucleic acid(s), and by the presence or concentration of formamide, tetramethylammonium chloride or other solvent(s) in a hybridization mixture.

The presently disclosed cartridges allow for precise, individualized temperature control, thus, nucleic acids of interest can also be amplified using a variety of known amplification techniques. For instance, polymerase chain reaction (PCR) technology may be used to amplify target sequences directly from DNA, RNA, or cDNA. In some embodiments, the assay surface is coated with a primer that hybridizes to the target sequence, and the reagents can include amplification regents, e.g., an opposing complementary primer, polymerase, buffers, etc. Once thermocycling is complete, excess reagent can be washed through the cartridge by wash reagent, optionally followed by a detection reagent.

F. Kits

Further provided are kits that include the presently disclosed assay cartridges. For example, a cartridge can be included with a kit that further includes reagents and components for common clinical or research assays. In some embodiments, the kit includes a cartridge with containers pre-filled with assay reagents. In some embodiments, the kit includes a cartridge and assay reagents in separate containers to be added to the cartridge to carry out the desired assay. In some embodiments, the kit further includes wash or buffer solutions (e.g., concentrated stock solutions, or dry buffer components for hydration). In some embodiments, the kit includes a plurality of coverslips, e.g., as a supply to be coated with sample or reagent by the user. In some embodiments, the kit includes controls for the assay (e.g., a coverslip known to be positive or negative for the targeted analyte).

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded.

The above disclosure is provided to illustrate the invention but not to limit its scope. Variants of the invention will be readily apparent to one of ordinary skill in the art and are encompassed by the appended claims. All publications, databases, internet sources, patents, patent applications, and accession numbers cited herein are hereby incorporated by reference in their entireties for all purposes. To the extent such documents incorporated by reference contradict the disclosure contained in the specification, the specification is intended to supersede and/or take precedence over any contradictory material.

What is claimed is:

1. A cartridge comprising:
   a block frame comprising:
   (a) a well, wherein the well comprises an outlet, at least one inlet, and a bottom surface;
   (b) a plurality of containers embedded in the block frame, wherein each container is connected to the well via a microchannel leading to the at least one inlet; and
   (c) a trough separate from and surrounding the well, said trough configured to hold a liquid; and
   an openable cover, which cover when closed is configured to enclose an assay surface and form a gap between (i) the assay surface and the bottom surface of the well or (ii) the assay surface and the cover.

2. The cartridge of claim 1, wherein the outlet leads from the bottom surface of the well.

3. The cartridge of claim 1, wherein the at least one inlet leads to the bottom surface of the well.

4. The cartridge of claim 1, wherein the gap is formed by a spacer, wherein the spacer extends from the bottom surface of the well, and is configured to meet the cover or assay surface on the outer edge of the cover or assay surface; hold the cover or assay surface parallel to the bottom surface of the well; and leave an opening on a side of the gap between the cover or assay surface and the bottom surface of the well through which liquid can pass.

5. The cartridge of claim 1, wherein the gap is formed by a spacer, wherein the spacer extends from the outer edge of the cover, and is configured to meet the bottom surface of the well and leave an opening between the cover and the bottom surface through which liquid can pass when the cover is closed.

6. The cartridge of claim 5, wherein the assay surface, when present, is placed inside the spacer on the bottom surface of the well.

7. The cartridge of claim 1, wherein each of the plurality of containers is attached to a valve-operated inlet channel.

8. The cartridge of claim 1, wherein each of the plurality of containers is connected to the well via a microchannel leading to a separate inlet.

9. The cartridge of claim 1, further comprising the assay surface.

10. The cartridge of claim 9, wherein the assay surface faces the gap and is coated with cells, antibodies, protein, or nucleic acids.

11. The cartridge of claim 1, further comprising a thermal element underlying the bottom surface of the well.

12. The cartridge of claim 1, further comprising at least one container embedded in the cover.

* * * * *